(12) United States Patent
Fraser (10) Patent No.: US 6,464,634 B1
(45) Date of Patent: Oct. 15, 2002

(54) SURGICAL RETRACTOR SYSTEM

(75) Inventor: Robert D. Fraser, Myrtle Bank (AU)

(73) Assignee: Depuy Acromed, Inc., Raynham, MA (US)

( * ) Notice: Subject to any disclaimer, the term of this patent is extended or adjusted under 35 U.S.C. 154(b) by 0 days.

(21) Appl. No.: 09/671,046

(22) Filed: Sep. 27, 2000

(51) Int. Cl.$^7$ .............................................. A61B 1/32
(52) U.S. Cl. ................................................ 600/233
(58) Field of Search ............................. 600/201, 206, 600/210, 219, 227, 228, 230, 231, 232, 233, 234; D24/135

(56) References Cited

U.S. PATENT DOCUMENTS

| | | | |
|---|---|---|---|
| 2,586,488 A | * | 2/1952 | Smith .......................... 600/233 |
| 3,038,468 A | * | 6/1962 | Raeuchle ...................... 600/233 |
| 3,998,217 A | * | 12/1976 | Trumbull et al. ............. 128/20 |
| 4,254,763 A | | 3/1981 | McCready et al. |
| 4,421,108 A | | 12/1983 | Cabrera et al. |
| 4,424,724 A | | 1/1984 | Bookwalter et al. |
| 4,467,791 A | | 8/1984 | Cabrera et al. |
| 4,945,897 A | * | 8/1990 | Greenstein et al. ........... 128/20 |
| 5,052,373 A | | 10/1991 | Michelson |
| 5,052,374 A | * | 10/1991 | Alvarez-Jacinto ............ 128/20 |
| D343,235 S | * | 1/1994 | LeVahn ..................... D24/135 |
| 5,280,782 A | | 1/1994 | Wilk |
| 5,375,481 A | | 12/1994 | Cabrera et al. |
| 5,520,608 A | | 5/1996 | Cabrera et al. |
| 5,616,117 A | | 4/1997 | Dinkler et al. |
| 5,893,831 A | | 4/1999 | Koros et al. |
| 5,967,974 A | * | 10/1999 | Nicholas et al. ............. 600/233 |
| 6,196,969 B1 | * | 3/2001 | Bester et al. ................ 600/224 |

* cited by examiner

Primary Examiner—Eduardo C. Robert
(74) Attorney, Agent, or Firm—Nutter McClennen & Fish LLP (57) ABSTRACT

A surgical retractor system comprises a support frame and at least one retractor blade. The support frame has a generally horizontally oriented support member comprising a plurality of holes. The surgical retractor has at least one retractor blade which is mateable at a selected position on the support frame. At least one retractor blade of the surgical retractor system has an open access window which provides greater visual and physical access to the surgical field.

34 Claims, 8 Drawing Sheets

SURGICAL RETRACTOR SYSTEM

CROSS-REFERENCE TO RELATED APPLICATIONS

Not applicable.

STATEMENT REGARDING FEDERALLY SPONSORED RESEARCH

Not applicable.

FIELD OF THE INVENTION

The present invention relates to medical devices, in particular to a surgical retractor blade and system.

BACKGROUND OF THE INVENTION

Even with the advent of minimally invasive surgical techniques, many surgical procedures still require an exposed surgical field for the surgeon to successfully perform. Often, the greater the visibility and access a surgeon has to a surgical site, the greater the probability that a successful outcome will result. Once entry is made into a patient, soft tissue is dissected away further exposing the field. However, the exposed field must be maintained using instruments that do not obstruct either visual or physical access.

Surgical retractors are used to maintain exposure and access to a surgical field. There are a variety of retractors, and different surgical protocols require different styles of retractors. For example, in lumbar surgery the retractor needs to be strong enough to overcome the force exerted by the large muscle mass that has been dissected away from the field of exposure, while maintaining a visual field and access by the surgeon. Additionally, retractors are required to partition other soft-tissue components of the surgical field. This need has lead to retractor systems having solid blades connected to a firm blade-holding retractor frame. U.S. Pat. No. 5,520,608 discloses a curved, solid retractor blade useful for orthopaedic surgery.

During surgery, it is advantageous to have retractor blades that are removably attachable to a support frame. U.S. Pat. No. 4,421,108 is an example of a quick-release ratcheting holder for a surgical retractor. Other mechanisms for holding a retractor blade in position are disclosed in U.S. Pat. Nos. 4,424,724; 4,467,791; 5,375,481; 5,616,117; and 5,893,831.

Accordingly, there exists a need for greater flexibility in a surgical retractor system while improving both visual and physical access by the surgeon to the surgical field.

SUMMARY OF THE INVENTION

The present invention provides a surgical retractor blade and system useful for surgical procedures, including orthopaedic and spinal surgery. In one embodiment, the surgical retractor blade of the invention is used with a support frame that includes a horizontally oriented support member having a plurality of mounting holes. This surgical retractor system further includes at least one retractor blade which is mateable at a selected position on the support frame. The retractor blade includes an open access window that facilitates both visual and physical access to the surgical wound.

The retractor blade of the present invention has a substantially elongated, horizontally oriented mounting portion with a longitudinally extending slot formed therein. The retractor blade also comprises a tissue-retracting portion which is integral with and distal to the mounting portion. The tissue-retracting portion has a first section which is coplanar with the mounting portion, and a second section which is angularly oriented with respect to the first section. The open access window is substantially centrally formed, and it is present in both the first and second sections of the tissue-retracting portion of the retractor. The second section of the tissue-retracting position of the blade is preferably angularly oriented with respect to the first section. The angle of orientation is in the range of about 45° to 135°.

The retractor blade also comprises a fastening mechanism that effectively enables it to mate to the support frame in a desired position. In one embodiment, a mounting screw is used to mate the retractor blade to the support frame. Other fastening mechanisms, such as clamping devices, can also be used to fasten the retractor blade to the support frame.

The foregoing and other features and advantages of the present invention will be more fully understood from the following detailed description along with the accompanying drawings.

DETAILED DESCRIPTION OF THE INVENTION

Figure 1:
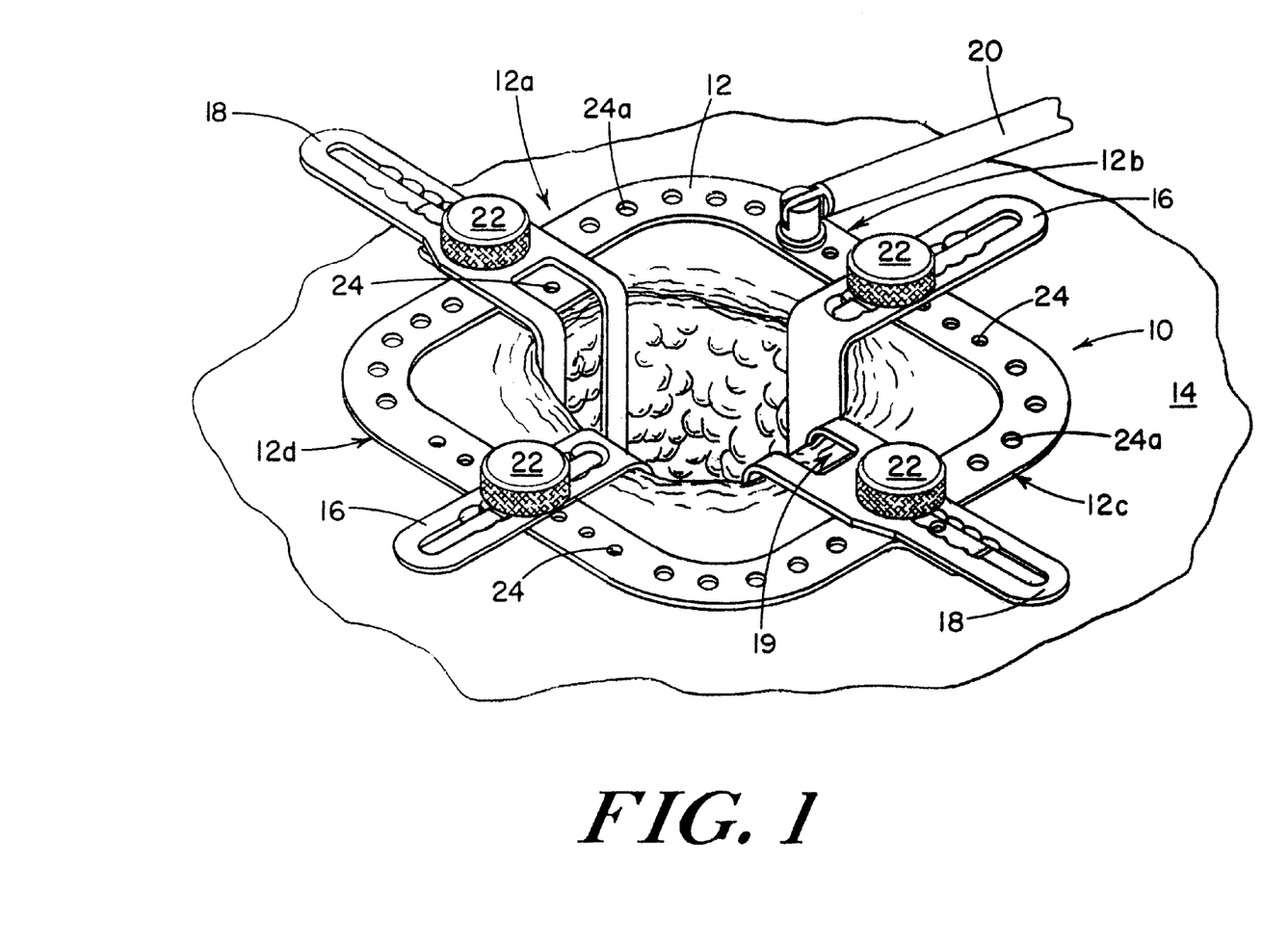
FIG. 1 is a perspective view of a surgical retractor system of the present invention in use during a surgical procedure.

Referring now to FIG. 1, there is shown a surgical retractor system 10 of the present invention. The retractor system 10 is attached to an operating table (not shown) in a manner well known to those having ordinary skill in the art. The retractor system 10 includes a frame 12, which is preferably suspended above the patient 14, common retractor blades 16, and retractor blades 18 having an access window 19. The system 10 may also include a supporting arm 20 which may be connected to a support post (not shown) or similar elements to affix and support the retractor system in a desired position.

With further reference to FIGS. 1 through 2B and 4, the retractor system 10 of the present invention further includes one or more fixation elements 22, such as thumb screws, that are effective to secure retractor blades 16, 18 to the frame 12 in a desired position so that tissue can be retracted. In one embodiment, the support frame 12 is a four-sided, substantially rectangular object having a central opening 21. Each side 12a, 12b, 12c, 12d of frame 12 includes one or more mounting holes 24, which preferably are internally threaded. The holes 24 are adapted to threadably mate with a threaded shaft 26 of fixation elements 22. Although shown as being substantially square or rectangular, it is understood that opposing sides 12a, 12b, 12c, 12d that form frame 12 need not be parallel. Thus, the frame may be in the form of a circle or an oval, or it may be substantially O-shaped or D-shaped.

Figure 2A:
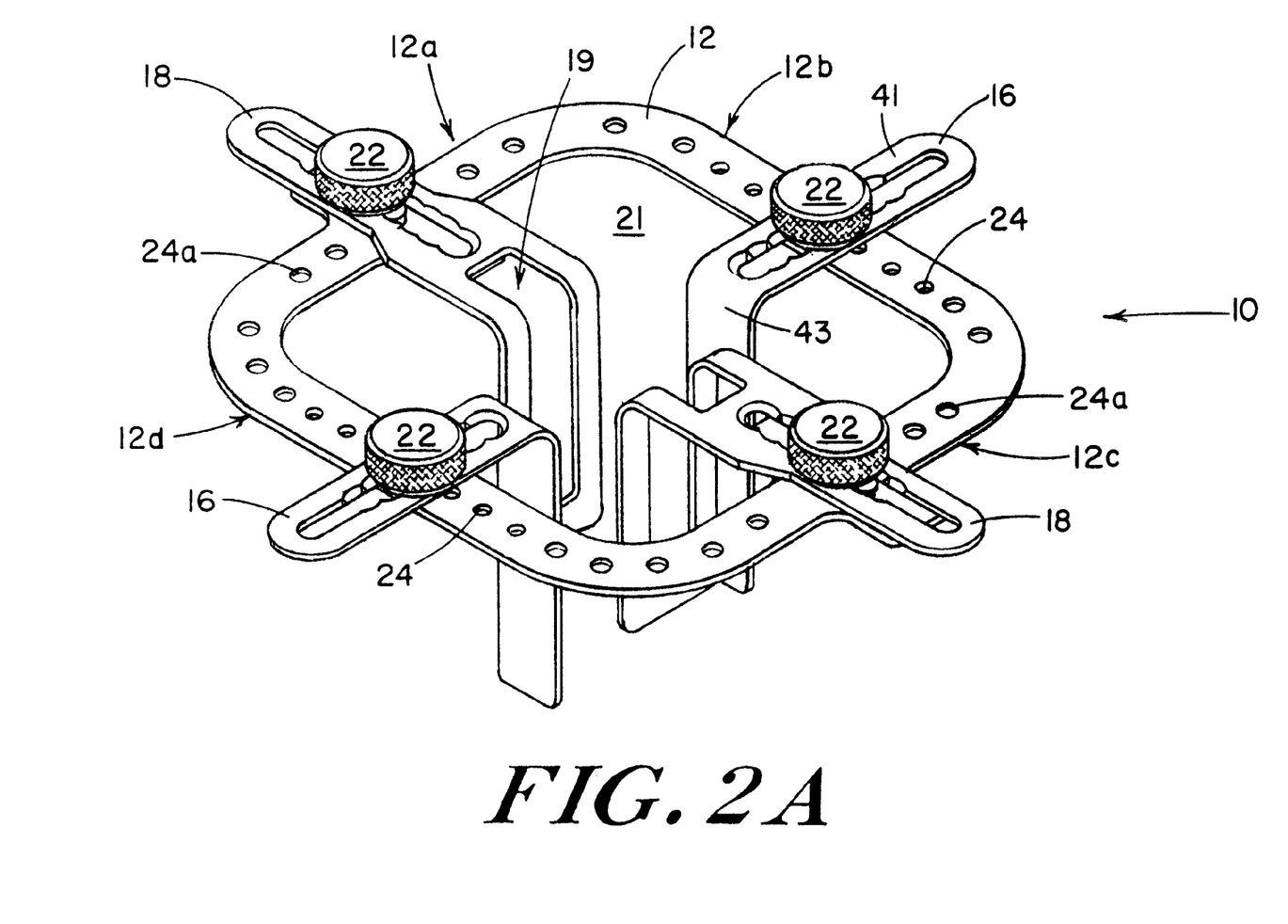
FIG. 2A is a perspective view of the surgical retractor system of FIG. 1.
Figure 2B:
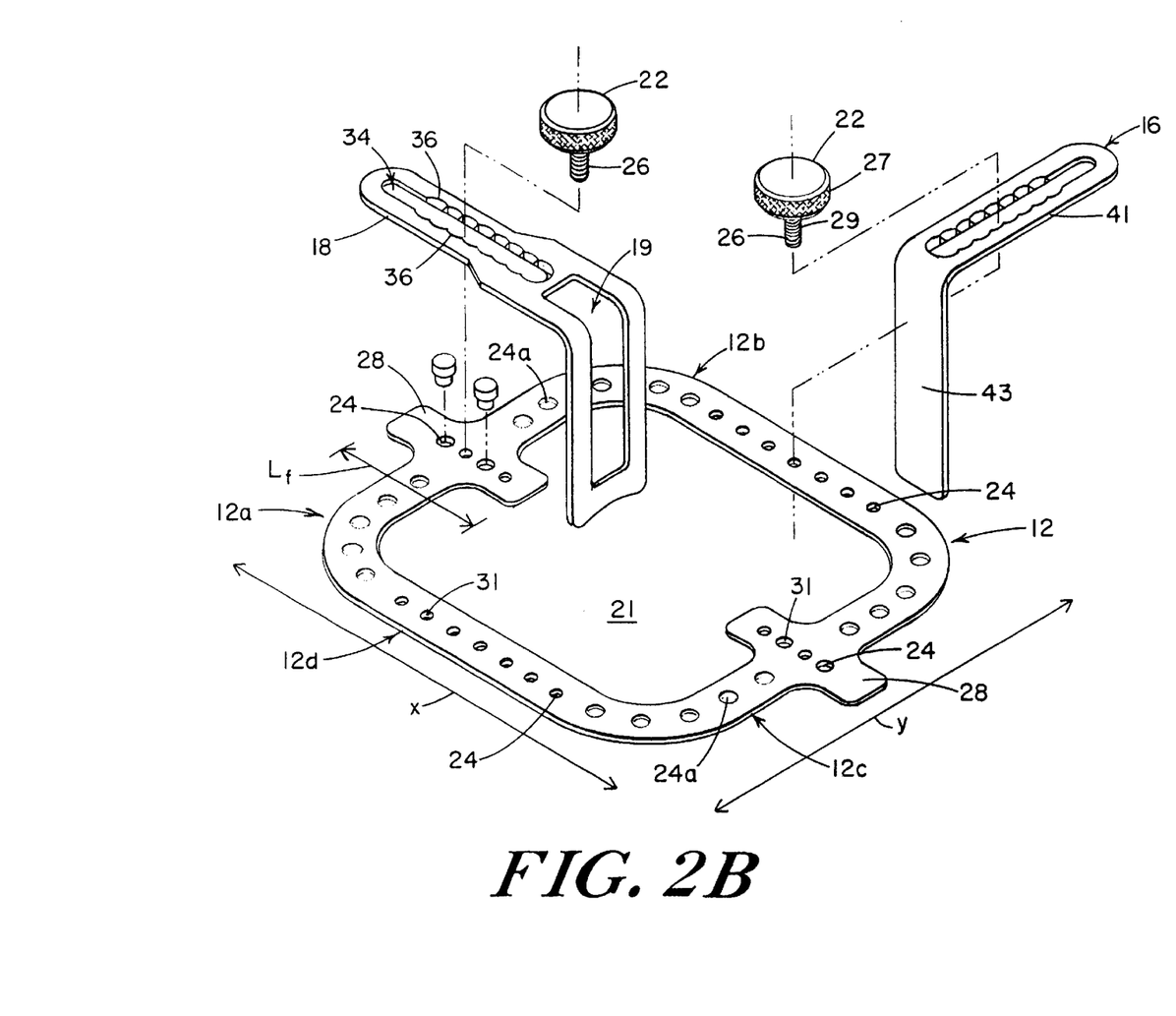
FIG. 2B is an exploded, disassembled view of the system shown in FIG. 2A.

In one embodiment, the mounting holes 24 formed in sides 12b and 12d are aligned so as to be parallel to the direction in which the sides 12b and 12d extend, enabling retractor blades 16 to be positioned at various locations along the length of sides 12b, 12d (in the x direction, as shown in FIG. 2B). As shown best in FIG. 2B, sides 12a and 12c each include flanges 28 that extend perpendicular to sides 12a, 12c, on either side of sides 12a, 12c. In this embodiment mounting holes 24 are disposed in flanges 28 such that the holes extend in a direction substantially parallel to the holes formed in sides 12b, 12d. The presence of the flange structure enables retractor blades 18 to be mounted securely on the frame 12 and to be positioned at various locations in the x direction (FIG. 2B). Optionally, additional mounting holes 24a may be present on sides 12a, 12c, extending in a direction parallel to that in which sides 12a, 12c are oriented. The presence of mounting holes 24a allows the blades 16, 18 to be located in various positions in the y direction. One of ordinary skill in the art will readily appreciate that the common retractor blades 16 and retractor blades 18 each may be mounted on sides 12a, 12b, 12c, or 12d.

The dimensions of frame 12 may vary as required by different surgical applications. The number and size of mounting holes 24 may vary as well. In one embodiment, the sides 12a–12d have a length and a range of about 100 to 500 mm. In one embodiment, the frame 12 may be square or rectangular, and the dimensions of central opening 21 are in the range of about 80 by 150 mm to about 300 by 450 mm. Flanges 28 preferably extend a distance $L_f$ of about 20 to 60 mm. The number of mounting holes 24 present in the sides and in the flanges 28 may vary as well. Generally, about 5–10 holes 24 and 24a are present in each of the sides while about 3–6 holes 24 are formed in the flanges 28. In one embodiment mounting holes may be placed entirely around the frame.

Figure 3A:
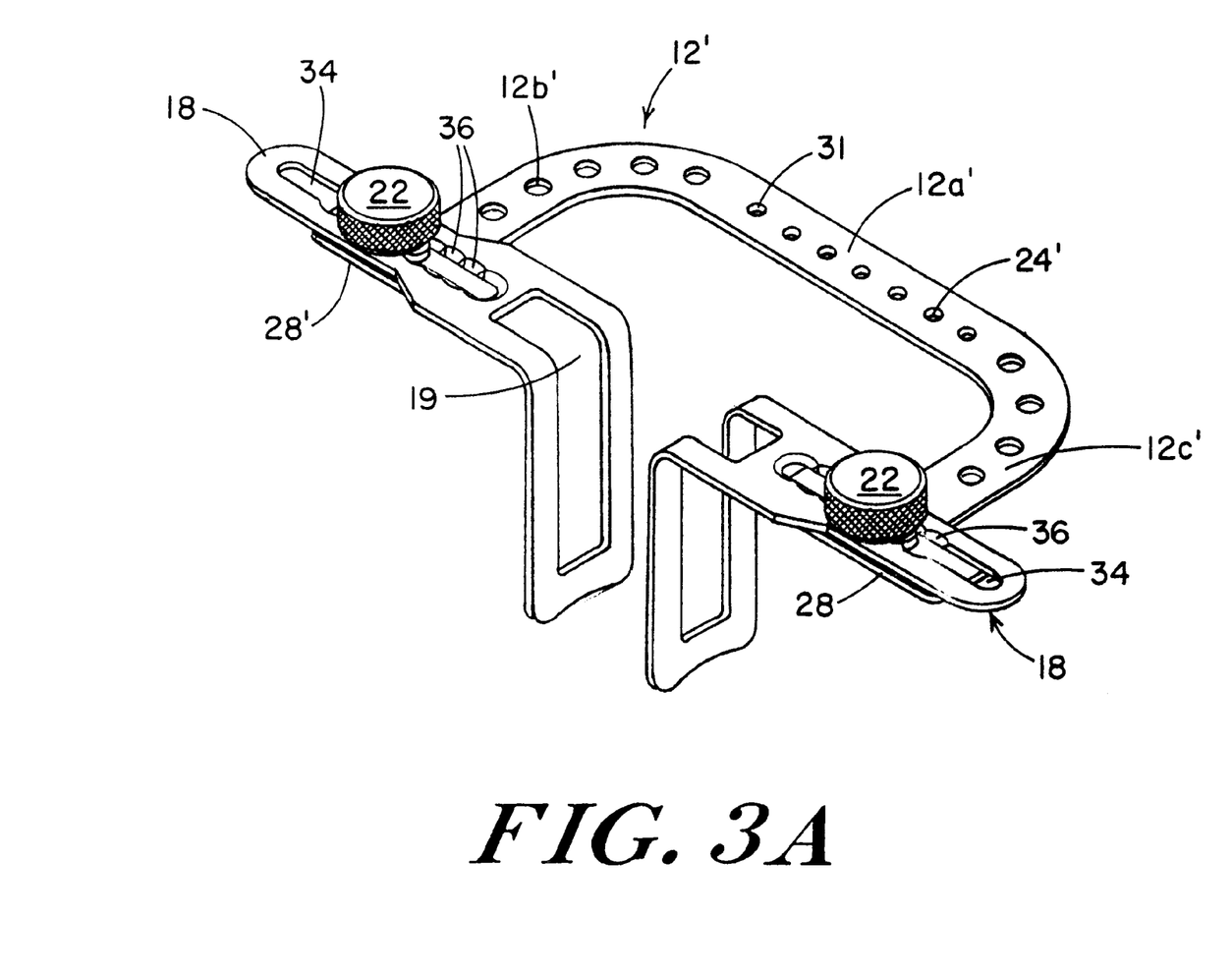
FIG. 3A is a perspective view of a surgical retractor system according to another embodiment of the invention.
Figure 3B:
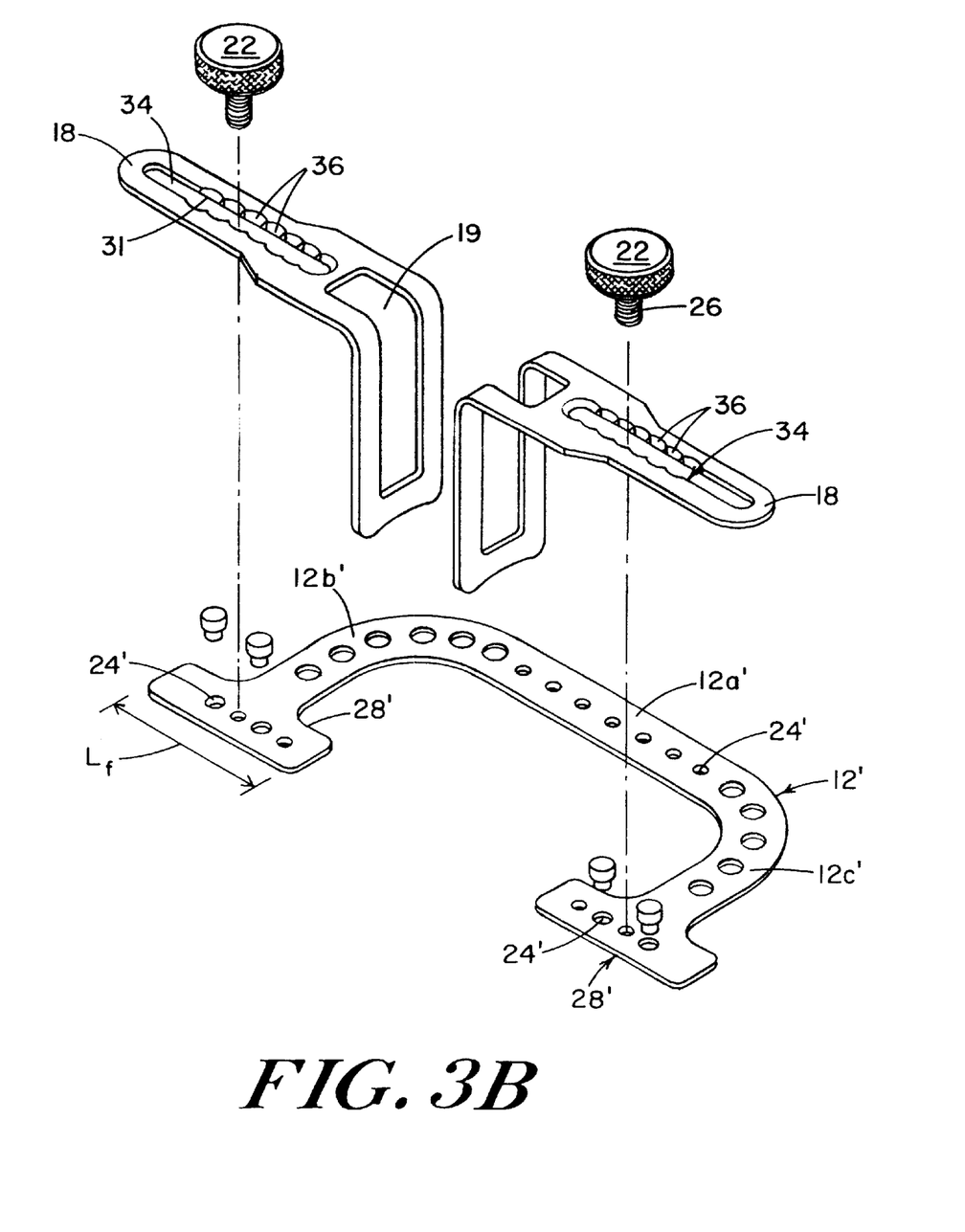
FIG. 3B is an exploded, disassembled view of the system shown in FIG. 3A.
Figure 4:
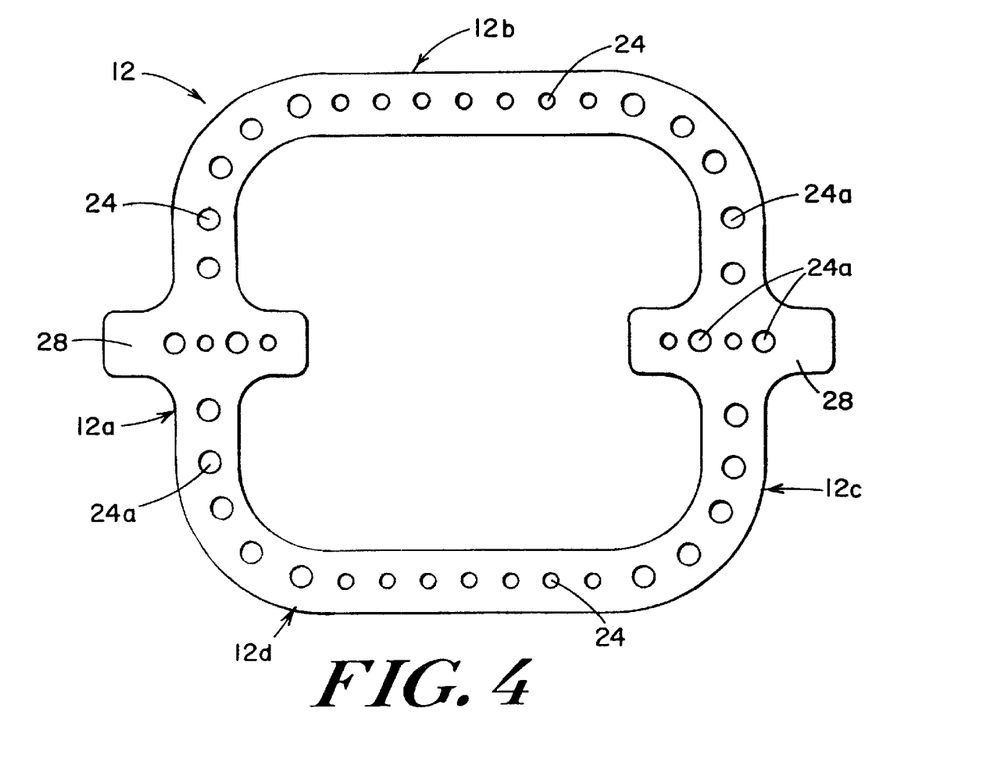
FIG. 4 is a plan view of a portion of the retractor system according to one embodiment of the invention.
Figure 5:
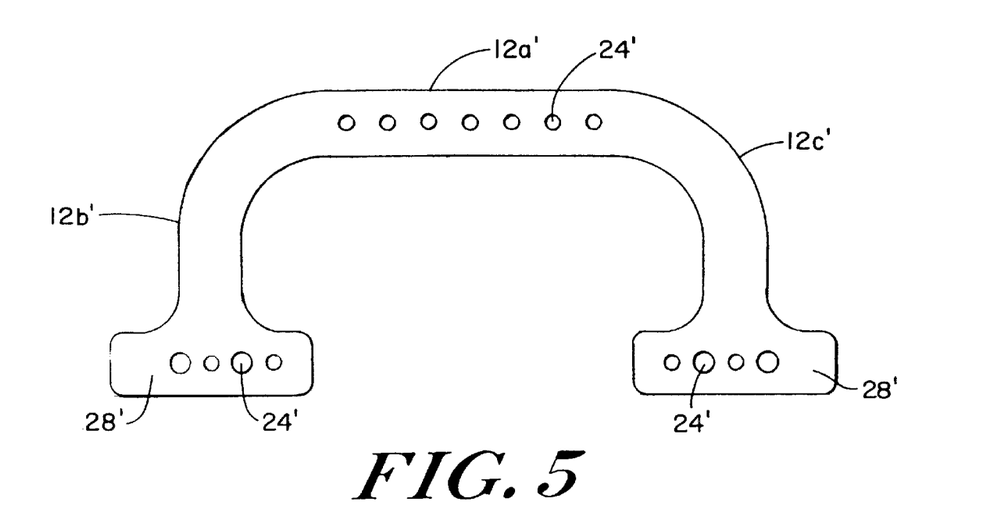
FIG. 5 is a plan view of a portion of the retractor system according to another embodiment of the invention.

FIGS. 3A, 3B, and 5 illustrate an alternative embodiment in which frame 12' is a three-sided member, which can be characterized as being substantially C-shaped. As illustrated, frame 12' has a long side 12a' and opposed shorter sides 12b' and 12c'. The long side 12a' preferably includes a number of mounting holes 24' that are oriented in a direction parallel to the side 12a'. The shorter sides 12b', 12c ' each include flanges 28' that extend in a direction parallel to side 12a'. The flanges 28' preferably include a number of holes 24' that are oriented in a direction parallel to the holes formed in side 12a'.

One of ordinary skill in the art will appreciate that the dimensions of frame 12' may vary as well. The length of side 12a' is in the range of about 150 to 500 mm while the length of sides 12b', 12c' is in the range of about 100 to 300 mm. The length $L_f$ of flanges 28' may be similar to that of flanges 28. In addition, one of ordinary skill in the art will appreciate that flanges 28' may include the same as or a different number of holes as are present in flanges 28.

The common retractor blades 16 may be of a type that includes a mounting section 41 and a tissue-retracting section 43. The mounting section is substantially horizontally oriented and the tissue-retracting section 32 is angularly oriented with respect to the mounting section. The tissue-retracting section 32 may be oriented at an angle of about 45° to 135° with respect to the mounting section, and preferably at an angle of about 90°. The mounting section 30 further includes a slot 34 having screw nesting positions 36 as will be described below with respect to retractor blade 18. As described above, the orientation of the holes on sides 12b and 12d (assuming one opts to mount blades 16 on sides 12b and 12d) allows blades 16 to be mounted in various locations in the x direction. The position of blades 16 in the y direction can be controlled by the positioning of the screw nesting positions 36 of slot 34 with respect to fastening element 22.

The fixation elements 22 are used to secure the mounting portion 18 of a blade 16, 18 to the frame 12. For purposes of illustration, the fixation elements 22 are shown as thumb screws, having a head 27 and a shaft 26. Preferably, the shaft 26 has external threads 29, enabling the fixation element to mate with internal threads 31 formed in mounting holes 24, 24a. One of ordinary skill in the art will understand that the shaft 26 of the fixation element must be appropriately sized to fit within the mounting holes 24.

Figure 6A:
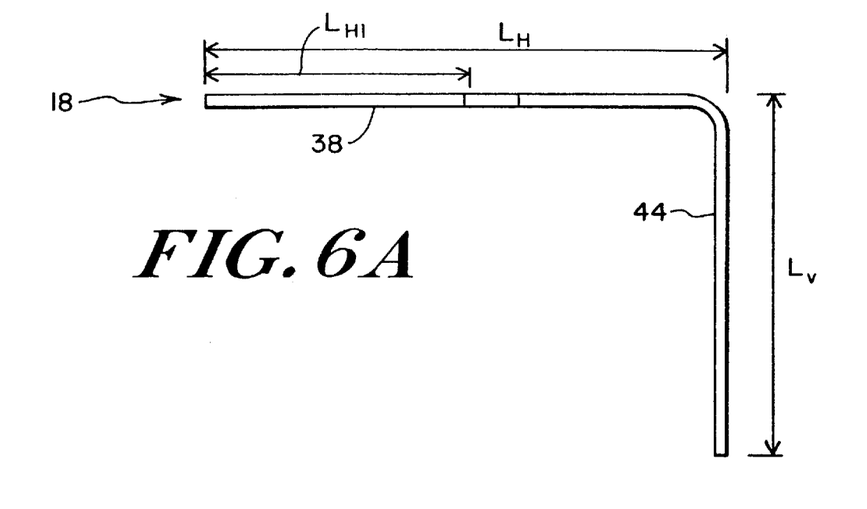
FIG. 6A is a side elevational view of a retractor blade useful with the present invention.
Figure 6B:
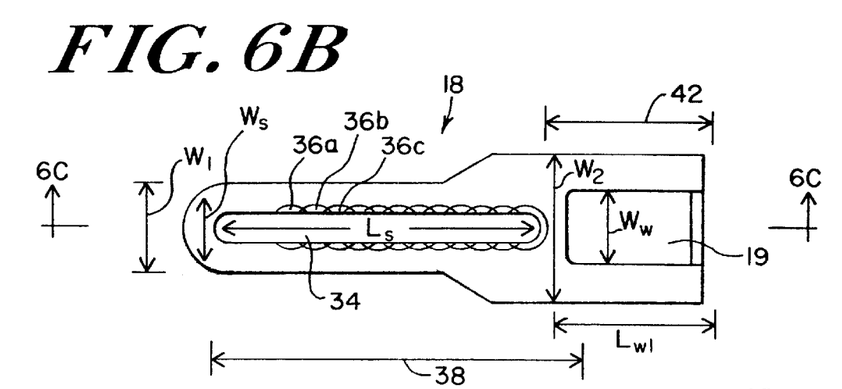
FIG. 6B is a plan view of the retractor blade of FIG. 6A.
Figure 6C:
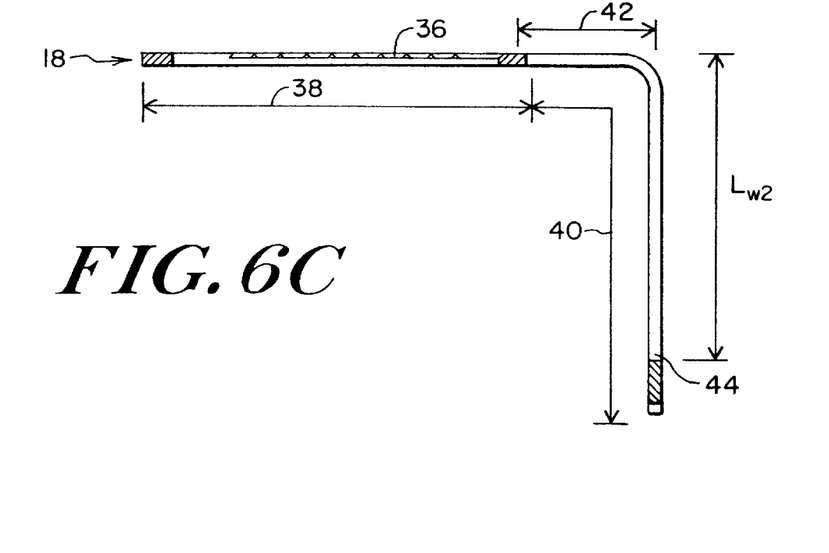
FIG. 6C is a sectional view of the retractor blade of FIG. 6B at lines 6C—6C.
Figure 7:
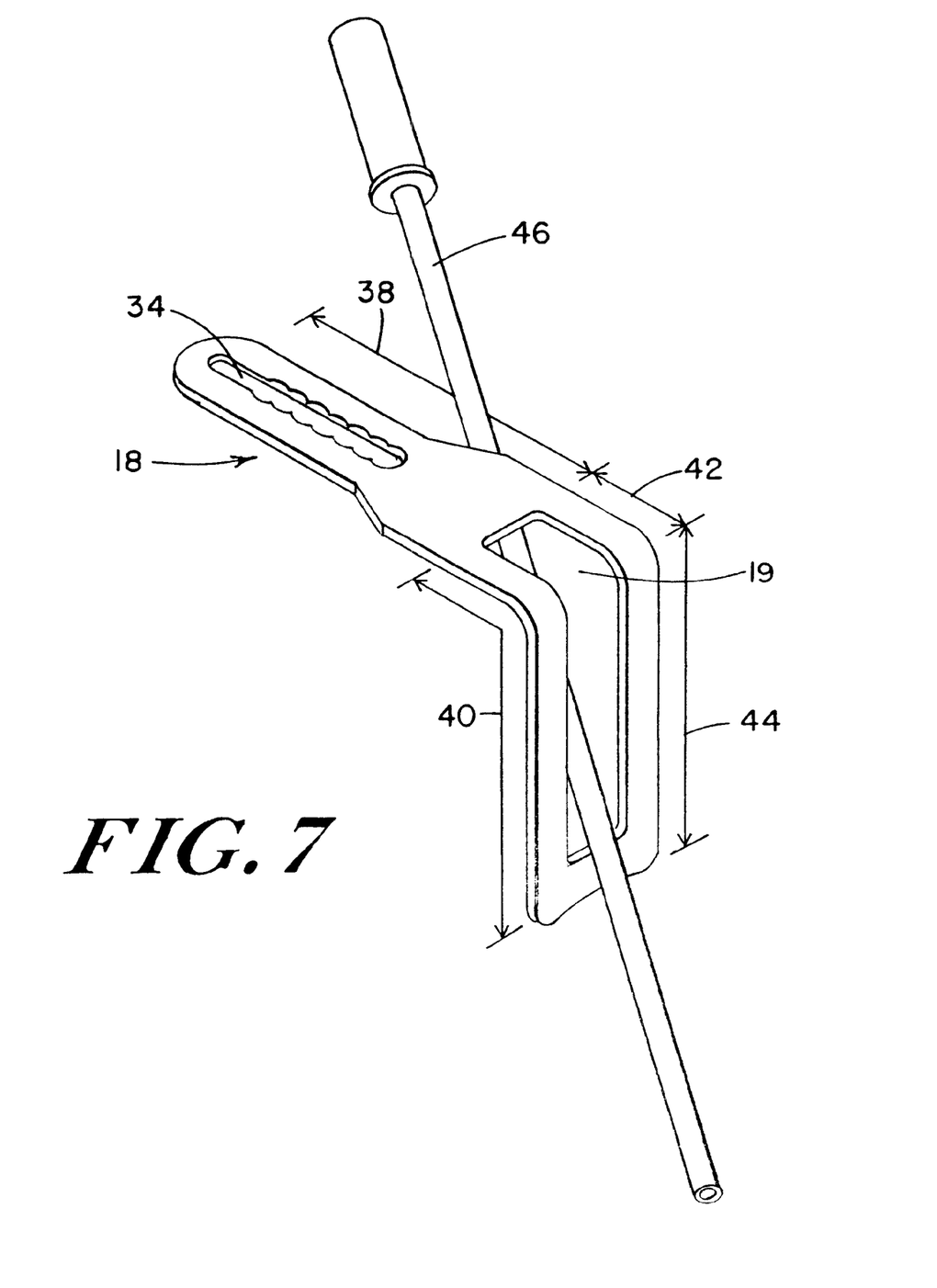
FIG. 7 is a perspective view of a retractor blade according to the present invention, together with a surgical tool.

The retractor blades 18 of the present invention include features that allow tissue to be effectively retracted while increasing the surgeon's visual and physical access to the surgical site. With reference to FIGS. 6A–7, the blades 18 have a mounting portion 38 which, for reference purposes, is substantially horizontally oriented, and an adjacent tissue-retracting portion 40. The mounting portion 38 includes an elongate slot 34. In one embodiment, the elongate slot 34 has a scalloped perimeter that defines multiple screw seating positions 36. That is, as is best shown in FIGS. 6B and 6C, the slot 34 includes multiple adjacent screw seating positions 36a, 36b, 36c.

The tissue-retracting portion 40 of blade 18 includes a first section 42 that is coplanar with the mounting portion 38 and a second section 44 that is angularly oriented with respect to the first section. An open access window 19 is formed in both the first and second sections 42, 44 of the tissue-retracting portion 40. Preferably, the access window 19 is substantially centrally positioned within the first and second sections 42, 44. In one embodiment at least a portion of either or both of the mounting or tissue-retracting portions 38, 40 is malleable to enable a surgeon to optimize the shape of the blade for the best performance in tissue retraction. Selective malleability can be achieved by material choice and/or by utilizing a thinner material in a region or regions ("bend zone") where malleability is desired.

As noted above, the second section 44 of the tissue-retracting portion 40 of plate 18 is angularly oriented with respect to the first section 42. The angle of orientation may be in the range of about 45° to 135°, and preferably this angle is about 90°. In an embodiment in which the blade is malleable, the angular orientation may be selectively altered by a surgeon.

The access window 19 spans both the first and second sections 42, 44 of the tissue-retracting portion 40 and thus is three dimensional, as shown in FIG. 7. The access window 19 can be characterized as being substantially rectangular in shape, having both a generally horizontal (formed in the first section 42) and a generally vertical portion (formed in the second section 44).

One of ordinary skill in the art will appreciate that the dimensions of the retractor blade 18 may vary upon the desired surgical applications. Referring to FIGS. 6A–6C, the length of a horizontally extending portion $L_H$ of the blade 18 is in the range of about 40 to 300 mm while the length of a vertically extending section $L_v$ is in the range of about 15 to 100 mm. The length of the tissue retracting portion is in the range of about 20 to 200 mm. The width of the blade at a widest section ($W_2$) may be in the range of about 30 to 200 mm. As illustrated, one segment of the mounting portion 38 of the blade 18 may be slightly narrower than the width $W_2$. This width dimension ($W_1$) is in the range of about 10 to 100 mm and extends over a majority of the mounting portion 38 of the blade. The length of the narrower segment of the mounting portion, defined by $L_{H1}$ in FIG. 6A, is in the range of about 20 to 250 mm.

As noted above, the slot 34 is elongate and generally has a length ($L_s$) in the range of about 20 to 200 mm. The width of the slot ($W_s$) is preferably in the range of about 3 to 10 mm.

The access window 19 preferably has a width ($W_w$) in the range of about 5 to 90 mm. The length of the access window in the first section 42 of the tissue retraction portion 40 ($L_{w1}$) is in the range of about 15 to 195 mm while the length ($L_{w2}$) of the access window in the second section 44 of the tissue retraction portion 40 is in the range of about 40 to 300 mm. The length ($L_v$) of the second section 44 of the tissue-retracting portion 40 is about 20 to 250 mm.

FIG. 7 schematically illustrates an advantage of the retractor blade 18 of the present invention. While the blade 18 is effective, in concert with other blades, to retract tissue, visual and physical access by the surgeon is enhanced as a result of the access window 19. That is, a surgical tool 46 is able to be passed through the access window to a desired location, or to further retract or otherwise manipulate tissue that is adjacent to the access window.

One of ordinary skill in the art will appreciate that the components of the retractor system of the present invention can be made from one or more biocompatible metals or metal alloys, or polymeric materials. An exemplary metal is titanium, while exemplary alloys include, but are not limited to, stainless steel (e.g., 316 LVM stainless steel), a titanium-vanadium-aluminum alloy (e.g., an alloy having about 90% by weight titanium, about 6% by weight aluminum, and about 4% by weight vanadium), a cobalt-chromium alloy, a cobalt-chromium-molybdenum alloy and a cobalt-nickel-chromium-molybdenum alloy. Biocompatible polymeric materials are also included within the instant invention. Examples of such polymers include nylons, polyetheretherketones (PEEK), polyetheraryl ketones (PEAK), and polysulfones.

One of ordinary skill in the art will appreciate further features and advantages of the invention based on the above-described embodiments. Accordingly, the invention is not limited by what has been particularly shown and described, except as indicated by the appended claims. Although dimensions are provided, it is understood that these dimensions may vary and are provided for purposes of exemplification. All patents and publications cited herein are expressly incorporated by reference in their entirety.

What is claimed is:

1. A surgical retractor system, comprising:
   a support frame having a generally horizontally oriented support member with at least two horizontally oriented sides, each side of the support member having a plurality of mounting holes formed therein and extending along at least a portion of the length thereof, each mounting hole being adapted to receive a fastening element;
   at least one retractor blade, mateable at a selected position on the support frame, the at least one retractor blade having
   a substantially elongate, horizontally oriented mounting portion having formed therein a longitudinally extending slot, and
   a tissue-retracting portion integral with and distal to the mounting portion, the tissue-retracting portion having a first section coplanar with the mounting portion, a second section angularly oriented with respect to the first section, and an open access window substantially centrally formed in both the first and second sections of the tissue retracting portion, the second section of the tissue-retracting portion forming a closed distal end around the open access window; and
   at least one fastening element effective to selectively mate one of the at least one retractor blades to the support frame at one of the plurality of mounting holes.

2. The system of claim 1, wherein the support frame is a four sided, substantially rectangular member having an open interior portion.

3. The system of claim 2, wherein each of the four sides of the frame are integral with each other and the mounting holes are formed in each side and are adjacent to each other.

4. The system of claim 3, wherein at least one side of the frame has a mounting flange integral therewith, and the mounting flange is oriented in a direction substantially perpendicular to the side of the frame with which it is integral.

5. The system of claim 4, wherein the frame has first and second mounting flanges, each integral with opposite sides of the frame.

6. The system of claim 5, wherein each mounting flange has mounting holes formed therein, and the mounting holes extend and are formed adjacent to each other in a pattern that is parallel to the mounting flange.

7. The system of claim 6, wherein each of the first and second mounting flanges has a length in the range of about 20 mm to 60 mm.

8. The system of claim 1, wherein at least part of the mounting portion has a width in the range of about 30 to 200 mm.

9. The system of claim 1, wherein the slot has a length in the range of about 20 to 200 mm and a width in the range of about 3 to 10 mm.

10. The system of claim 1, wherein the first section of the tissue retracting portion has a width in the range of about 30 to 100 mm.

11. The system of claim 10, wherein the combined length of the mounting portion and the first section of the tissue retracting portion is in the range of about 40 to 300 mm.

12. The system of claim 1, wherein the length of the second section of the tissue retracting portion is in the range of about 20 to 250 mm.

13. The system of claim 1, wherein the open access window extends continuously from the first section to the second section of the tissue retracting portion.

14. The system of claim 13, wherein length of the open access window in the first section of the tissue retracting portion is in the range of about 15 to 195 mm.

15. The system of claim 13, wherein the length of the open access window in the second section of the tissue retracting portion is in the range of about 40 to 300 mm.

16. The system of claim 1, wherein the second section of the tissue retracting portion extends at an angle of about 90° with respect to the first section of the tissue retracting portion.

17. The system of claim 1, wherein the at least one fastening element is a thumbscrew.

18. The system of claim 1, wherein the slot has a scalloped perimeter defining multiple screw seating positions.

19. The system of claim 1, wherein at least a portion of each of the at least one retractor blades is malleable.

20. The surgical retractor system of claim 1, wherein the support member includes at least one side, and the plurality of mounting holes are disposed substantially along a length of the at least one side, each mounting hole defining a selected position along the at least one side of the support frame.

21. A surgical retractor system; comprising:

a substantially C-shaped support frame having a generally horizontally oriented support member having formed therein a plurality of mounting holes adapted to receive a fastening element, and having a long side with mounting holes formed therein adjacent to each other and spaced along the long side in a pattern parallel to the long side, and first and second short sides extending from opposite sides of the long side, wherein each short side having at least one mounting hole formed therein;

at least one retractor blade, mateable at a selected position on the support frame, the at least one retractor blade having a substantially elongate, horizontally oriented mounting portion having formed therein a longitudinally extending slot, and a tissue-retracting portion integral with and distal to the mounting portion, the tissue-retracting portion having a first section coplanar with the mounting portion, a second section angularly oriented with respect to the first section, and an open access window substantially centrally formed in both the first and second sections of the tissue retracting portion; and at least one fastening element effective to selectively mate one of the at least one retractor blades to the support frame at one of the plurality of mounting holes.

22. The system of claim 21, wherein a plurality of mounting holes are formed in the short sides of the frame and extend in a pattern substantially perpendicular to the mounting holes formed in the long side of the frame.

23. The system of claim 21, wherein each of the first and second short sides has a mounting flange integral therewith and oriented substantially parallel to the long side.

24. The system of claim 23, wherein each mounting flange has mounting holes formed therein, and the mounting holes extend and are formed adjacent to each other in a pattern that is parallel to the mounting flange.

25. A surgical retractor system, comprising:

a support frame having a generally horizontally oriented support member having formed therein a plurality of mounting holes adapted to receive a fastening element, the mounting holes including internal threads;

at least one retractor blade, mateable at a selected position on the support frame, the at least one retractor blade having a substantially elongate, horizontally oriented mounting portion having formed therein a longitudinally extending slot, and a tissue-retracting portion integral with and distal to the mounting portion, the tissue-retracting portion having a first section coplanar with the mounting portion, a second section angularly oriented with respect to the first section, and an open access window substantially centrally formed in both the first and second sections of the tissue retracting portion; and at least one fastening element effective to selectively mate one of the at least one retractor blades to the support frame at one of the plurality of mounting holes.

26. A surgical retractor system, comprising:

a support frame having a generally horizontally oriented support member having formed therein a plurality of mounting holes adapted to receive a fastening element;

at least one retractor blade, mateable at a selected position on the support frame, the at least one retractor blade having a substantially elongate, horizontally oriented mounting portion having formed therein a longitudinally extending slot, and a tissue-retracting portion integral with and distal to the mounting portion, the tissue-retracting portion having a first section coplanar with the mounting portion, a second section angularly oriented with respect to the first section, and an open access window substantially centrally formed in both the first and second sections of the tissue retracting portion; and at least one fastening element effective to selectively mate one of the at least one retractor blades to the support frame at one of the plurality of mounting holes, the at least one fastening element comprising a mounting screw having a head and a threaded shaft.

27. A surgical retractor blade, comprising:

a substantially flat, elongate first portion extending in a first orientation, the first portion including a slot having one or more positions effective to mate with a fastening element; and a substantially flat, elongate second portion integral with the first portion, the second portion having a first section extending in the first orientation, a second section extending in a second orientation, and only one access window extending between the first and second sections, the second section of the elongate second portion forming a closed distal end around the access window.

28. The blade of claim 27, wherein the positions effective to mate with a fastening element are present in a mounting slot formed in the first portion of the blade.

29. The blade of claim 27, wherein the slot has a scalloped perimeter defining multiple positions effective to mate with a fastening element.

30. The blade of claim 27, wherein the second portion is adapted to engage and retract tissue.

31. The blade of claim 27, wherein the first orientation is horizontal and the second orientation is vertical.

32. The blade of claim 27 wherein the second portion is angularly oriented with respect to the first portion.

33. The blade of claim 32, wherein the second section of the second portion is oriented with respect to the first portion at an angle in the range of about 45° to 135°.

34. The blade of claim 33, wherein the slot is elongate.

* * * * *